United States Patent [19]

Panoz et al.

[11] Patent Number: 4,820,521

[45] Date of Patent: * Apr. 11, 1989

[54] SUSTAINED ABSORPTION PHARMACEUTICAL COMPOSITION

[75] Inventors: Donald E. Panoz; Edward J. Geoghegan, both of Athlone, Ireland

[73] Assignee: Eland Corporation P.L.C., Athlone, Ireland

[*] Notice: The portion of the term of this patent subsequent to May 5, 2004 has been disclaimed.

[21] Appl. No.: 3,736

[22] Filed: Jan. 16, 1987

Related U.S. Application Data

[63] Continuation of Ser. No. 870,293, May 21, 1986, Pat. No. 4,663,150, which is a continuation of Ser. No. 597,716, Apr. 6, 1984, abandoned.

[30] Foreign Application Priority Data

Apr. 16, 1983 [IE] Ireland .................................. 789/83

[51] Int. Cl.$^4$ .......................... A61K 9/52; A61K 9/22; A61K 9/26; A61K 31/52
[52] U.S. Cl. .................................... 424/458; 424/470; 514/273
[58] Field of Search ................. 514/273; 424/470, 458

[56] References Cited

U.S. PATENT DOCUMENTS

| | | | |
|---|---|---|---|
| 2,853,420 | 9/1958 | Lowey | 167/82 |
| 3,080,294 | 3/1963 | Shepard | 167/82 |
| 3,081,233 | 3/1963 | Euz et al. | 167/82 |
| 3,109,775 | 11/1963 | Shepard et al. | 167/82 |
| 3,247,066 | 4/1966 | Milosovich | 167/82 |
| 3,344,029 | 9/1967 | Berger | 167/82 |
| 3,400,185 | 9/1968 | Kohnle et al. | 264/117 |
| 3,835,221 | 2/1974 | Fulberth et al. | 424/20 |
| 3,906,087 | 9/1975 | Sim et al. | 424/22 |
| 3,949,068 | 4/1976 | Polin | 424/79 |
| 4,016,254 | 4/1977 | Seager | 424/33 |
| 4,083,949 | 4/1978 | Benedikt | 424/19 |
| 4,085,214 | 4/1978 | Higuchi et al. | 424/253 |
| 4,173,626 | 11/1979 | Dempski et al. | 424/19 |
| 4,248,858 | 2/1981 | Guley et al. | 424/21 |
| 4,309,406 | 1/1982 | Guley et al. | 424/21 |
| 4,324,779 | 4/1982 | Dalhausen et al. | 424/20 |
| 4,367,217 | 1/1983 | Gruber et al. | 424/19 |
| 4,415,547 | 11/1983 | Yu et al. | 424/19 |
| 4,462,991 | 7/1984 | Higuchi et al. | 424/177 |
| 4,663,150 | 5/1987 | Panoz et al. | 514/263 |
| 4,710,384 | 12/1987 | Rotman | 424/470 |

FOREIGN PATENT DOCUMENTS

| | | |
|---|---|---|
| 1178204 | 11/1984 | Canada . |
| 0032562 | 7/1981 | European Pat. Off. . |
| 0036145 | 9/1981 | European Pat. Off. . |
| 0069958 | 1/1983 | European Pat. Off. . |
| 0092060 | 10/1983 | European Pat. Off. . |
| 83/00284 | 2/1983 | PCT Int'l Appl. . |
| 2025227 | 1/1980 | United Kingdom . |
| 2067073A | 7/1981 | United Kingdom . |

OTHER PUBLICATIONS

Rohm Pharma GmbH "Eudragit RL/RS".
"Pharmaceutical Dosage Forms" Edited by Liebermann and Lachman (1980), p. 434.

*Primary Examiner*—Shep K. Rose
*Attorney, Agent, or Firm*—Hubbard, Thurman, Turner & Tucker

[57] ABSTRACT

A sustained absorption theophylline-containing pellet for oral administration comprises a core of theophylline or a pharmacological equivalent thereof and an organic acid embedded in a polymeric material in a multi-layer arrangement and an outer membrane which permits release of the theophylline at a controlled rate in an aqueous medium. The pellet has a dissolution rate in vitro in an aqueous medium, which when measured in a basket assembly according to U.S. Pharmacopoeia XX at 37° C. and 75 r.p.m., is not more than 15% of the total theophylline after 2 hours of measurement in a buffer solution at pH 7.5. Not more than 35% of the total theophylline is released after a total of 7 hours of measurement and not more than 65% of the total theophylline is released after a total of 13 hours.

17 Claims, 1 Drawing Sheet

SUSTAINED ABSORPTION PHARMACEUTICAL COMPOSITION

This application is a continuation of application Ser. No. 870,293, filed May 21, 1986, now U.S. Pat. No. 4,663,150, which is a continuation of application Ser. No. 597,716 filed Apr. 6, 1984, now abandoned.

BACKGROUND OF THE INVENTION

1. Field of the Invention

This invention relates to sustained absorption pharmaceutical compositions and, in particular, to a sustained absorption theophylline composition.

2. Description of the Prior Art

Theophylline (1,3-dimethylxanthine) has a pharmacological activity similar to that of the other xanthine derivatives, caffeine and theobromine. The diuretic action of theophylline though stronger than that of caffeine is of short duration. Theophylline is a more powerful relaxant of involuntary muscle than either theobromine or caffeine. Theophylline is primarily used as a bronchosphasm relaxant or bronchodilator in bronchosphasm associated with asthma, chronic bronchitis and emphysema.

Theophylline has been found to have a minimum effective plasma concentration of about 5 mcg/ml and an average therapeutic concentration of about 10 mcg/ml. The therapeutic range of concentration of theophylline is generally regarded in practice as 10-20 mcg/ml, levels below 10 mcg/ml being ineffective and levels above 20 mcg/ml being toxic.

The apparent biological half-life of theophylline has been found to range from 4-9 hours.

Preparations of anhydrous theophylline require a dosage regimen of 150-500 mg orally every six hours for adults.

For this reason, a number of slow or sustained release forms of theophylline have been developed and include: THEOGRAD, which is marketed by Abbott Laboratories Limited and comes in 350 mg tablets and is administered at a rate of one tablet per 12 hours; THEO-DUR, marketed by Fisons Limited and which comes in 200 mg and 300 mg tablets and is administered 12 hourly, initially 200-300 mg, increasing by 100-150 mg until a sufficient therapeutic effect is obtained; and UNIPHYLLIN UNICONTIN, marketed by Napp Laboratories Limited which comes in 200 mg tablets, with three or four tablets being taken as a single daily dose, following initial therapy of two daily given as a once or twice daily dosage with subsequent increments as necessary until a sufficient therapeutic effect is obtained.

With each slow-release form of theophylline the dose is increased until the required therapeutic effect is obtained, this is known as a titration standard.

An effective slow or sustained release form of theophylline suitable for once daily administration must be capable of maintaining the plasma concentration of theophylline within the range of 10-20 mcg/ml over 24 hours. Only a product with a Cmax/Cmin at 24 hours ratio of 2:1 or less could maintain levels within this range 24 hours after administration.

It is an object of the present invention to provide a sustained absorption form of theophylline which is suitable for once daily administration and which gives a consistent Cmax/Cmin ratio at 24 hours of 2:1 or less.

DESCRIPTION OF THE PREFERRED EMBODIMENTS

Accordingly, the invention provides a sustained absorption active ingredient-containing pellet for oral administration, said pellet comprising a core of an active ingredient selected from the group consisting of anhydrous theophylline, aminophylline, dyphylline, theophylline calcium salicylate and theophylline sodium glycinate and an organic acid selected from the group consisting of citric acid, tartaric acid, succinic acid, malic acid, ascorbic acid and fumaric acid or a mixture thereof embedded in a polymeric material which contains a major proportion of a water-soluble polymer and membrane of a film-forming polymer or mixture thereof surrounding the core whereby said active ingredient is released at a controlled rate in an aqueous medium and said pellet has a dissolution rate in an aqueous medium which is substantially independent of pH and which when measured in a Basket Assembly according to U.S. Pharmacopoeia XX at 37° C. and 75 r.p.m., in a buffer solution at pH 7.5 has the following characteristics:

(a) from 0 to 15% of said active ingredient is released after two hours of measurement in said assembly;
(b) from 15 to 35% of said active ingredient is released after 7 hours of measurement in said assembly;
(c) from 45 to 65% of said active ingredient is released after 13 hours of measurement in said assembly; and
(d) from 80 to 100% of said active ingredient is released after 24 hours of measurement in said assembly.

As used herein "theophylline" means theophylline or a derivative or salt thereof. Suitable forms of theophylline for use in the pellets according to the invention are anhydrous theophylline, aminophylline, dyphylline, theophylline calcium salicylate and theophylline sodium glycinate.

Preferably, the organic acid is selected from one or more of the following acids: citric acid, tartaric acid, succinic acid, malic acid, ascorbic acid and fumaric acid.

The theophylline and organic acid are preferably present in a ratio of 4:1.

Preferably, the polymeric material in which the theophylline is embedded includes a major proportion of a water-soluble polymer.

The polymeric material may consist solely of a water soluble polymer or, alternatively, it may include a minor proportion of a water insoluble polymer. Suitably, the water soluble and water insoluble polymers will be present in a ratio of 9:1.

The water soluble polymer is suitably hydroxypropylmethylcellulose, polyvinylpyrrolidone or a polymer sold under the trade mark EUDRAGIT RL. Polymers sold under the Trade Mark EUDRAGIT are acrylic resins comprising co-polymers of acrylic and methacrylic acid esters with a low content of quaternary ammonium groups and are described in the "Eudragit" brochure of Rohm Pharma GmbH (1982) wherein detailed physical-chemical data of these products is given. The ammonium groups are present as salts and give rise to permeability of the lacquer films. Eudragit RL and RS are freely permeable (RL) or slightly permeable (RS), respectively independent of pH.

The water insoluble polymer is suitably a cellulose ether such as methyl-, ethyl- or propylcellulose, shellac or a polymer sold under the trade mark EUDRAGIT RS. Shellac is a resinous excretion of the insect Laccifer (Tachardia) Lacca Kerr, order Homoptera, family Coccidae.

The core will suitably have between 20 and 120 layers and is built up in a manner known per se.

Further, preferably, the multi-layer arrangement of theophylline, organic acid and polymeric material will be built up on a central inert core suitably consisting of a non-pareil seed having an average diameter in the range 0.3-0.7 mm.

The membrane preferably includes a major proportion of a water insoluble polymer.

Further, the membrane suitably comprises a major proportion of a water insoluble polymer and a minor proportion of a water soluble polymer, the ratio of water insoluble to water soluble polymer being determined by the inherent solubility characteristics of the polymers selected.

Suitable combinations of water insoluble and water soluble polymers for the membrane include: ethylcellulose and hydroxypropylmethylcellulose in a ratio of 9:1; EUDRAGIT RS and EUDRAGIT RL in a ratio of 8:2 and shellac and polyvinylpyrrolidone in a ratio of 9:1.

The pellets may be filled into hard gelatin capsules or compressed into tablets using a binder and/or hardening agent commonly employed in tabletting such as microcrystalline cellulose sold under the trade mark AVICEL or a co-crystallized powder of highly modified dextrins (3% by weight) and sucrose sold under the trade mark DI-PAC, in such a way that the specific dissolution rate of the pellets is maintained.

The invention will be further illustrated by the following Examples.

EXAMPLE 1

Theophylline-containing pellets were prepared in the following manner.

(a) Powder Blend

Anhydrous theophylline (#100 mesh)(3,500 g), talc (438 g) and citric acid (875 g) were blended in a standard pharmaceutical blender into a uniform powder.

(b) Polymer Solution

A solution of 5% hydroxypropylmethylcellulose in methanol/methylene chloride, 60:40 was prepared.

(c) Membrane Solution

The membrane solution was prepared from the following ingredients:
One part (by volume) 10% hydroxypropylmethylcellulose (15 c.p.s.) in methanol/methylene chloride, 60:40;
Nine parts (by volume) 10% ethylcellulose (50 c.p.s.) in methanol/methylene chloride, 60:40;
Ten parts (by volume) methanol/methylene chloride, 60:40;
Ten parts (by weight) talc;
Diethylphthalate (plasticizer), as required.

Pellet Making Procedure

Step 1. 500 g of starch/sugar seeds (0.4 to 0.5 mm diameter) were placed in a conventional coating pan and rotation was commenced.

Step 2. The seeds were wetted with sufficient polymer solution (b) to dampen them uniformly.

Step 3. Powder blend (a) was dusted on until no more adhered to the dampened seeds.

Step 4. The powder coated seeds were allowed to dry (5-15 minutes).

Steps 2-4 were repeated until all of the powder (a) had been coated on.

Step 5. The powder coated seeds were sealed with one application of polymer solution (b) and talc.

Step 6. The powder coated seeds were dried at 45°-50° C. for at least 12 hours.

Step 7. The powder coated seeds were placed in a conventional coating pan and rotation was commenced.

Step 8. A coat of membrane solution (c) was applied to the powder coated seeds and the seeds so coated were allowed to dry. A coat of membrane solution (c) corresponds to 10 ml of solution (c) per 1,000 g of coated seeds.

Step 9. Two further coats of membrane solution (c) were applied to the coated seeds.

Step 10. The finished pellets were allowed to dry at 45°-50° C.

The dired pellets were subjected to a dissolution test as follows:

Apparatus:
A Basket Assembly as described in the United States Pharmacopoeia XX at 37° C. and 75 r.p.m.

Buffer:
25 ml of 2.0M potassium chloride and 950 ml of water was adjusted to pH 7.5 with either 0.1N hydrochloric acid or 0.1N sodium hydroxide and the volume made up to 1,000 ml with water.

Sampling Times:
2, 7, 13 and 24 hours.

Method:
1 g of finished pellets was placed in the basket of the assembly and rotation was commenced in the buffer. At the sampling times, 1.0 ml of the solution was removed and diluted to 50 ml with 0.1M hydrochloric acid. The absorbance of the sample was measured at 270 nm in a spectrophotometer.

The absorbance value equivalent to 100% dissolution was determined by grinding 1 g of pellets in 0.1M hydrochloric acid, diluting to 1,000 ml with water, further diluting a 1 ml sample to 50 ml with water and reading at 270 nm as above. The percentage dissolution was calculated by division.

Steps 7 to 10 were repeated until the dissolution rate at pH 7.5 was as follows:

| 2 hours  | 0-15%   |
| 7 hours  | 15-35%  |
| 13 hours | 45-65%  |
| 24 hours | 80-100% |

EXAMPLE 2

Theophylline-containing pellets were prepared in the following manner.

(a) Powder Blend

Anhydrous theophylline (#100 mesh)(3,500 g), talc (438 g) and tartaric acid (875 g) were blended in a standard pharmaceutical blender into a uniform powder.

(b) Polymer Solution

A solution of nine parts 6.25% EUDRAGIT RL in isopropanol/acetone, 60:40 and one part 6.25% EUDRAGIT RS in isopropanol/acetone, 60:40 was prepared.

(c) Membrane Solution

The membrane solution was prepared from the following ingredients:
Two parts (by volume) 5% EUDRAGIT RL in isopropanol/acetone, 60:40;
Eight parts (by volume) 5% EUDRAGIT RS in isopropanol/acetone, 60:40;
Ten parts (by volume) isopropanol/acetone, 60:40;
Ten parts (by weight) talc;
Diethylphthalate (plasticizer), as required.

Pellet Making Procedure

Steps 1–4 were carried out as in Example 1.
Steps 2–4 were repeated until all of the powder (a) had been coated on.
Step 5. The powder coated seeds were sealed with two applications of polymer solution (b) and talc.
Steps 6–8 were carried out as in Example 1. As in the case of Example 1 a coat of membrane solution (c) corresponds to 10 ml of solution (c) per 1,000 g of coated seeds.
Step 9. One further coat of membrane solution (c) was applied to the coated seeds.
Step 10. the finished pellets were allowed to dry at 45°–50° C.

The dried pellets were subjected to a dissolution test as described in Example 1 and Steps 7–10 were repeated until the desired dissolution rate at pH 7.5 was obtained.

EXAMPLE 3

Theophylline-containing pellets were prepared in the following manner.

(a) Powder Blend

Anhydrous theophylline (#100 mesh)(3,500 g), talc (438 g) and succinic acid (875 g) were blended in a standard pharmaceutical blender into a uniform powder.

(b) Polymer Solution

A solution of 10% polyvinylpyrrolidone in isopropanol was prepared.

(c) Membrane Solution

The membrane solution was prepared from the following ingredients:
One part (by volume) 20% polyvinylpyrrolidone (Kollidon K-30) in isopropanol;
Nine parts (by volume) 33% Shellac (dewaxed) in ethanol;
Ten parts (by volume) isopropanol;
Ten parts (by weight) talc;
Diethylphthalate (plasticizer), as required.

Pellet Making Procedure

Steps 1–4 were carried out as in Example 1.
Steps 2–4 were repeated until all of the powder (a) had been coated on.
Steps 5–10 were carried out as in Example 1.
The dried pellets were then subjected to a dissolution test as described in Example 1 above. In addition, the dissolution rate was also measured at pH 3.0 and pH 6.0. Steps 7–10 were repeated until a satisfactory dissolution rate was obtained at each pH. A total of 20 coats of membrane solution (c) was applied before the required dissolution rate was obtained.

Table 1 gives the percentage dissolution observed at each pH after 15, 17, 18 and 20 coats of membrane solution (c) had been applied.

TABLE 1

| Membrane Coats Applied | Time (h) | Dissolution (%) pH 3.0 | 6.0 | 7.5 |
| --- | --- | --- | --- | --- |
| 15 | 2 | 14 | 17 | 17 |
|  | 7 | 60 | 66 | 68 |
|  | 13 | 95 | 98 | 100 |
|  | 24 | 100 | 100 | 100 |
| 17 | 2 | 10 | 10 | 11 |
|  | 7 | 40 | 43 | 45 |
|  | 13 | 76 | 80 | 84 |
|  | 24 | 100 | 100 | 100 |
| 18 | 2 | 6 | 8 | 7 |
|  | 7 | 35 | 42 | 39 |
|  | 13 | 67 | 73 | 71 |
|  | 24 | 100 | 100 | 100 |
| 20 | 2 | 5 | 7 | 7 |
|  | 7 | 25 | 28 | 30 |
|  | 13 | 52 | 56 | 58 |
|  | 24 | 86 | 90 | 94 |

It will be observed from Table 1 that the pecentage dissolution at pH 3.0 and 6.0 at each sampling time were within 8% of the corresponding figure obtained at pH 7.5. Accordingly, it will be appreciated that the dissolution rate of the pellets according to the invention is substantially pH independent.

Figure 1:
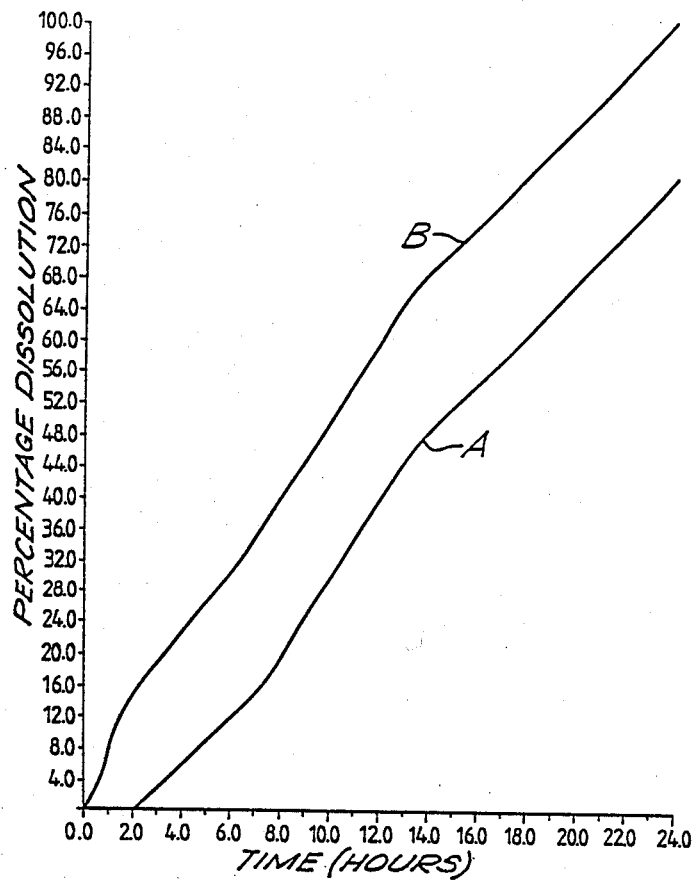
FIG. 1 is a graph of percentage dissolution versus time of pellets according to the invention. Curve B shows the maximum percentage dissolution per unit time and curve A the minimum percentage dissolution per unit time permissible to achieve the desired plasma concentration Cmax/Cmin at 24 hours of 2:1 or less.
Figure 2:
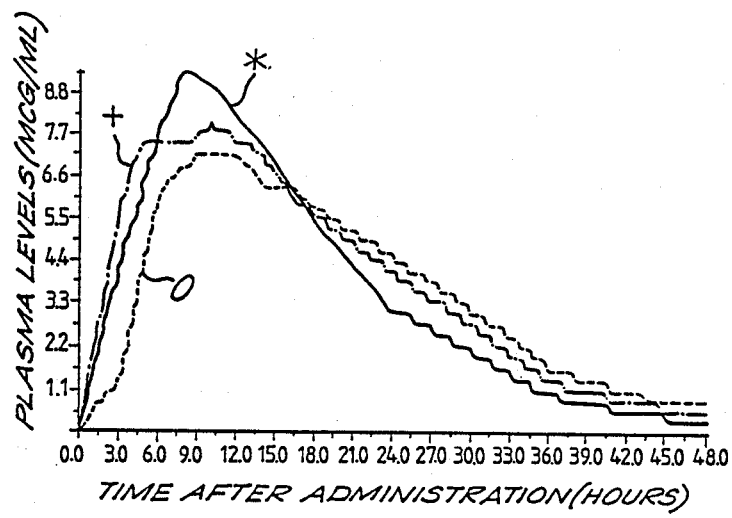
FIG. 2 is a graph of plasma levels (mcg/ml) versus time after administration (hours) for pellets prepared according to Example 3 (o) compared with two sustained release forms of theophylline currently on the market, namely THEO-DUR tablets (*) and UNIPHYLLIN UNICONTIN tablets (+).

The graphs of FIG. 2 were drawn from the mean values obtained for six subjects according to the data listed in Tables 2, 3 and 4.

TABLE 2

Sustained-absorption theophylline pellets prepared according to Example 3
Blood level study results - Summary of pharmacokinetic data

| SUBJ | Plasma Levels (mcg/ml) HOURS AFTER ADMINISTRATION | | | | | | | | | | | | | | | AUC** |
| --- | --- | --- | --- | --- | --- | --- | --- | --- | --- | --- | --- | --- | --- | --- | --- | --- |
|  | 0.00 | 3.00 | 4.00 | 5.00 | 6.00 | 8.00 | 10.00 | 11.00 | 12.00 | 13.00 | 14.00 | 16.00 | 24.00 | 36.00 | 48.00 |  |
| 1 | 0.00 | 1.67 | 2.64 | 3.38 | 4.24 | 6.70 | 6.86 | 6.71 | 7.02 | 6.04 | 6.36 | 6.62 | 6.36 | 3.69 | 1.64 | 219.54 |
| 2 | 0.00 | 1.12 | 1.76 | 3.04 | 5.06 | 5.99 | 6.86 | 7.62 | 7.38 | 7.15 | 7.49 | 6.59 | 4.13 | 1.36 | 0.51 | 163.91 |
| 3 | 0.00 | 1.37 | 1.85 | 2.95 | 3.82 | 4.41 | 4.44 | 4.72 | 5.25 | 5.31 | 4.32 | 5.30 | 4.82 | 1.10 | 0.00 | 138.41 |

TABLE 2-continued

Sustained-absorption theophylline pellets prepared according to Example 3
Blood level study results - Summary of pharmacokinetic data

| | | | | | | | | | | | | | | | | |
|---|---|---|---|---|---|---|---|---|---|---|---|---|---|---|---|---|
| 4 | 0.00 | 1.59 | 2.10 | 2.57 | 4.85 | 7.05 | 8.38 | 8.38 | 8.31 | 9.00 | 7.99 | 8.22 | 6.07 | 1.84 | 0.61 | 207.01 |
| 5 | 0.00 | 1.34 | 1.83 | 2.88 | 4.10 | 4.91 | 5.29 | 4.71 | 4.53 | 4.37 | 4.40 | 4.19 | 3.30 | 1.10 | 0.00 | 118.65 |
| 6 | 0.00 | 1.34 | 6.97 | 13.83 | 13.06 | 12.58 | 10.77 | 11.30 | 10.37 | 9.27 | 8.43 | 6.23 | 2.90 | 1.18 | 0.00 | 202.28 |
| MEAN | 0.00 | 1.41 | 2.86 | 4.78 | 5.86 | 6.94 | 7.10 | 7.24 | 7.14 | 6.86 | 6.50 | 6.19 | 4.60 | 1.71 | 0.46 | 174.97 |
| ST DEV | 0.00 | 0.20 | 2.04 | 4.44 | 3.56 | 2.94 | 2.26 | 2.49 | 2.11 | 1.99 | 1.79 | 1.36 | 1.42 | 1.01 | 0.64 | 40.96 |
| *CV (%) | 0.00 | 14.07 | 71.37 | 93.06 | 60.81 | 42.41 | 31.85 | 34.37 | 29.54 | 28.98 | 27.62 | 21.98 | 30.93 | 58.92 | 139.27 | 23.41 |
| MAX | 0.00 | 1.67 | 6.97 | 13.83 | 13.06 | 12.58 | 10.77 | 11.30 | 10.37 | 9.27 | 8.43 | 8.22 | 6.36 | 3.69 | 1.64 | 219.54 |
| MIN | 0.00 | 1.12 | 1.76 | 2.57 | 3.82 | 4.41 | 4.44 | 4.71 | 4.53 | 4.37 | 4.32 | 4.19 | 2.90 | 1.10 | 0.00 | 118.65 |

| MEAN OF CV VALUES AT SAMPLE POINTS | NUMBER OF ZERO BLOOD LEVELS | NUMBER OF POOR ABSORBERS** <10% AUC |
|---|---|---|
| 48.94 | 3 | 0 |

| | HOURS COVER AT FOUR BLOOD LEVELS | | | | PEAKING TIME | PEAK HEIGHT | C(MAX)/C(MIN) AT 24.00 HOURS |
|---|---|---|---|---|---|---|---|
| SUBJ | 0.00 | 5.00 | 10.00 | 20.00 | | | |
| 1 | 48.00 | 23.49 | 0.00 | 0.00 | 12.00 | 7.02 | 1.10 |
| 2 | 48.00 | 15.20 | 0.00 | 0.00 | 11.00 | 7.62 | 1.85 |
| 3 | 48.00 | 7.40 | 0.00 | 0.00 | 13.00 | 5.31 | 1.10 |
| 4 | 48.00 | 20.90 | 0.00 | 0.00 | 13.00 | 9.00 | 1.48 |
| 5 | 48.00 | 2.03 | 0.00 | 0.00 | 10.00 | 5.29 | 1.60 |
| 6 | 48.00 | 15.30 | 7.89 | 0.00 | 5.00 | 13.83 | 4.77 |
| MEAN | 48.00 | 14.05 | 1.32 | 0.00 | 10.67 | 8.01 | 1.98 |
| ST DEV | 0.00 | 8.10 | 3.22 | 0.00 | 3.01 | 3.18 | 1.40 |
| CV (%) | 0.00 | 0.58 | 2.45 | 0.00 | 0.28 | 0.40 | 0.70 |
| BASED ON MEAN BLOOD LEVEL CURVE | | | | | | | |
| MEAN | 48.00 | 16.77 | 0.00 | 0.00 | 11.00 | 7.24 | 1.58 |

*Coefficient of variation
**Area under the curve.

TABLE 3

Theo-Dur SR tablets
Blood level study results - Summary of pharmacokinetic data

Plasma Levels (mcg/ml)
HOURS AFTER ADMINISTRATION

| SUBJ | 0.00 | 3.00 | 4.00 | 5.00 | 6.00 | 8.00 | 10.00 | 11.00 | 12.00 | 13.00 | 14.00 | 16.00 | 24.00 | 36.00 | 48.00 | AUC** |
|---|---|---|---|---|---|---|---|---|---|---|---|---|---|---|---|---|
| 1 | 0.00 | 5.70 | 7.48 | 9.05 | 10.26 | 13.84 | 10.64 | 9.82 | 9.21 | 8.82 | 9.23 | 7.29 | 4.33 | 2.05 | 0.89 | 238.34 |
| 2 | 0.00 | 3.33 | 5.62 | 7.06 | 8.30 | 7.99 | 8.01 | 7.29 | 6.66 | 6.80 | 6.59 | 5.53 | 2.63 | 1.18 | 0.50 | 161.53 |
| 3 | 0.00 | 3.31 | 3.88 | 5.13 | 6.82 | 7.37 | 8.66 | 8.55 | 8.15 | 7.99 | 8.09 | 7.05 | 3.97 | 1.11 | 0.00 | 178.68 |
| 4 | 0.00 | 4.38 | 4.56 | 6.69 | 7.88 | 10.26 | 1.61 | 12.91 | 12.39 | 10.58 | 9.98 | 8.60 | 4.32 | 0.92 | 0.00 | 217.85 |
| 5 | 0.00 | 3.65 | 4.49 | 5.61 | 6.95 | 8.05 | 7.29 | 5.91 | 5.75 | 4.72 | 4.37 | 3.30 | 0.96 | 0.00 | 0.00 | 103.89 |
| 6 | 0.00 | 5.09 | 4.75 | 5.39 | 6.40 | 8.60 | 8.17 | 7.37 | 7.24 | 7.28 | 6.26 | 5.90 | 2.72 | 0.96 | 0.00 | 158.87 |
| MEAN | 0.00 | 4.24 | 5.13 | 6.49 | 7.77 | 9.35 | 9.06 | 8.64 | 8.23 | 7.70 | 7.42 | 6.28 | 3.16 | 1.04 | 0.23 | 176.53 |
| ST DEV | 0.00 | 0.99 | 1.28 | 1.47 | 1.41 | 2.41 | 1.68 | 2.47 | 2.36 | 1.97 | 2.08 | 1.82 | 1.32 | 0.66 | 0.38 | 47.64 |
| *CV (%) | 0.00 | 23.36 | 24.97 | 22.60 | 18.15 | 25.76 | 18.59 | 28.59 | 28.67 | 25.65 | 28.02 | 29.01 | 41.77 | 63.21 | 163.81 | 26.98 |
| MAX | 0.00 | 5.70 | 7.48 | 9.05 | 10.26 | 13.84 | 11.61 | 12.91 | 12.39 | 10.58 | 9.98 | 8.60 | 4.33 | 2.05 | 0.89 | 238.34 |
| MIN | 0.00 | 3.31 | 3.88 | 5.13 | 6.40 | 7.37 | 7.29 | 5.91 | 5.75 | 4.72 | 4.37 | 3.30 | 0.96 | 0.00 | 0.00 | 102.89 |

| MEAN OF CV VALUES AT SAMPLE POINTS | NUMBER OF ZERO BLOOD LEVELS | NUMBER OF POOR ABSORBERS <10% AUC |
|---|---|---|
| 38.73 | 5 | 0 |

| | HOURS COVER AT FOUR BLOOD LEVELS | | | | PEAKING TIME | PEAK HEIGHT | C(MAX)/C(MIN) AT 24.00 HOURS |
|---|---|---|---|---|---|---|---|
| SUBJ | 0.00 | 5.00 | 10.00 | 20.00 | | | |
| 1 | 48.00 | 19.56 | 5.00 | 0.00 | 8.00 | 13.84 | 3.20 |
| 2 | 48.00 | 13.73 | 0.00 | 0.00 | 6.00 | 8.30 | 3.16 |
| 3 | 48.00 | 16.43 | 0.00 | 0.00 | 10.00 | 8.66 | 2.18 |
| 4 | 48.00 | 18.52 | 6.19 | 0.00 | 11.00 | 12.91 | 2.99 |
| 5 | 36.00 | 8.27 | 0.00 | 0.00 | 8.00 | 8.05 | 8.39 |
| 6 | 48.00 | 14.19 | 0.00 | 0.00 | 8.00 | 8.60 | 3.16 |
| MEAN | 46.00 | 15.12 | 1.86 | 0.00 | 8.50 | 10.06 | 3.85 |
| ST DEV | 4.90 | 4.07 | 2.91 | 0.00 | 1.76 | 2.59 | 2.26 |
| CV (%) | 0.11 | 0.27 | 1.56 | 0.00 | 0.21 | 0.26 | 0.59 |
| BASED ON MEAN BLOOD LEVEL CURVE | | | | | | | |
| MEAN | 48.00 | 15.42 | 0.00 | 0.00 | 8.00 | 9.35 | 2.96 |

*Coefficient of variation
**Area under the curve

TABLE 4

Uniphylline Unicontin
Blood level study results - Summary of pharmacokinetic data Plasma Levels (mcg/ml)
HOURS AFTER ADMINISTRATION

| SUBJ | 0.00 | 4.00 | 4.00 | 5.00 | 6.00 | 8.00 | 10.00 | 11.00 | 12.00 | 13.00 | 14.00 | 16.00 | 24.00 | 36.00 | 48.00 | AUC** |
|---|---|---|---|---|---|---|---|---|---|---|---|---|---|---|---|---|
| 1 | 0.00 | 5.70 | 6.89 | 8.35 | 9.52 | 10.67 | 10.42 | 9.55 | 10.17 | 9.45 | 9.28 | 8.68 | 8.50 | 3.26 | 1.49 | 297.44 |
| 2 | 0.00 | 4.98 | 5.64 | 5.81 | 5.14 | 4.82 | 5.58 | 5.22 | 5.10 | 5.30 | 5.05 | 4.49 | 2.20 | 0.74 | 0.00 | 123.65 |
| 3 | 0.00 | 8.87 | 11.88 | 12.59 | 9.79 | 8.26 | 7.26 | 7.14 | 6.65 | 7.58 | 6.76 | 6.53 | 4.47 | 1.13 | 0.00 | 206.72 |
| 4 | 0.00 | 4.99 | 6.20 | 6.10 | 6.85 | 5.72 | 8.03 | 8.28 | 8.46 | 7.92 | 8.39 | 7.00 | 4.68 | 2.01 | 0.84 | 204.24 |
| 5 | 0.00 | 3.87 | 3.90 | 5.15 | 6.16 | 5.34 | 4.69 | 4.29 | 4.02 | 3.58 | 3.41 | 2.69 | 1.80 | 0.00 | 0.00 | 92.20 |
| 6 | 0.00 | 5.85 | 6.12 | 6.79 | 6.80 | 9.71 | 11.22 | 11.47 | 10.68 | 10.19 | 9.63 | 7.36 | 3.08 | 0.96 | 0.00 | 196.96 |
| MEAN | 0.00 | 5.71 | 6.77 | 7.47 | 7.38 | 7.42 | 7.87 | 7.66 | 7.51 | 7.34 | 7.09 | 6.13 | 4.12 | 1.35 | 0.39 | 186.87 |
| ST DEV | 0.00 | 17.0 | 2.70 | 2.74 | 1.87 | 2.47 | 2.59 | 2.69 | 2.71 | 2.50 | 2.48 | 2.17 | 2.44 | 1.14 | 0.64 | 72.09 |
| *CV (%) | 0.00 | 29.76 | 39.84 | 36.67 | 25.37 | 33.28 | 32.89 | 35.06 | 36.09 | 34.09 | 34.99 | 35.36 | 59.20 | 84.32 | 163.71 | 38.58 |
| MAX | 0.00 | 8.87 | 11.88 | 12.59 | 9.79 | 10.67 | 11.22 | 11.47 | 10.68 | 10.19 | 9.63 | 8.68 | 8.50 | 3.26 | 1.49 | 297.44 |
| MIN | 0.00 | 3.87 | 3.90 | 5.15 | 5.14 | 4.82 | 4.69 | 4.29 | 4.02 | 3.58 | 3.41 | 2.69 | 1.80 | 0.00 | 0.00 | 92.20 |

| MEAN OF CV VALUES AT SAMPLE POINTS | NUMBER OF ZERO BLOOD LEVELS | NUMBER OF POOR ABSORBERS <10% AUC |
|---|---|---|
| 48.62 | 5 | 0 |

| | HOURS COVER AT FOUR BLOOD LEVELS | | | | PEAKING TIME | PEAK HEIGHT | C(MAX)/C(MIN) AT 24.00 HOURS |
|---|---|---|---|---|---|---|---|
| SUBJ | 0.00 | 5.00 | 10.00 | 20.00 | | | |
| 1 | 48.00 | 29.38 | 4.16 | 0.00 | 8.00 | 10.67 | 1.26 |
| 2 | 48.00 | 9.55 | 0.00 | 0.00 | 5.00 | 5.81 | 2.64 |
| 3 | 48.00 | 20.25 | 2.55 | 0.00 | 5.00 | 12.59 | 2.82 |
| 4 | 48.00 | 19.89 | 0.00 | 0.00 | 12.00 | 8.46 | 1.81 |
| 5 | 36.00 | 4.17 | 0.00 | 0.00 | 6.00 | 6.16 | 3.42 |
| 6 | 48.00 | 17.85 | 4.96 | 0.00 | 11.00 | 11.47 | 3.72 |
| MEAN | 46.00 | 16.85 | 1.94 | 0.00 | 7.83 | 9.19 | 2.61 |
| ST DEV | 4.90 | 8.87 | 2.27 | 0.00 | 3.06 | 2.83 | 0.94 |
| CV (%) | 0.11 | 0.53 | 1.17 | 0.00 | 0.39 | 0.31 | 0.36 |
| | BASED ON MEAN BLOOD LEVEL CURVE | | | | | | |
| MEAN | 48.00 | 17.87 | 0.00 | 0.00 | 10.00 | 7.87 | 1.91 |

*Coefficient of variation
**Area under the curve

It was found that a 600 mg single dose of theophylline pellets prepared according to Example 3 in tablet form had a similar plasma level AUC (area under the curve) (175 mcg h/ml) as a 600 mg single dose of each of THEO-DUR (176.5 mcg h/ml) and UNIPHYLLIN UNICONTIN (186.9 mcg h/ml).

The theophylline prepared according to Example 3 had the lowest peak plasma level (Cmax) at the latest peak time (tmax) as shown in Table 5.

TABLE 5

| | Cmax (mcg/ml) | tmax (h) |
|---|---|---|
| Composition of Example 3 | 8.0 | 10.7 |
| THEO-DUR | 10.1 | 8.5 |
| UNIPHYLLIN UNICONTIN | 9.2 | 7.8 |

Furthermore, the theophylline prepared according to Example 3 showed the lowest single-dose peak to trough plasma concentration ratio (Cmax/Cmin at 24 hours); Composition according to Example 3=1.98; THEO-DUR=3.85; and UNIPHYLLIN UNICONTIN=2.61.

In terms of variability, the theophylline prepared according to Example 3 showed the lowest inter subject variability in plasma level AUC (area under the curve); Composition according to Example 3 % CV=23.4; THEO-DUR % CV=27.0; and UNIPHYLLIN UNICONTIN % CV=38.6.

It will be appreciated from the foregoing description that the pellets according to the invention are more readily absorbed than conventional sustained release forms of theophylline with a similar rate of release.

What we claim is:

1. A sustained absorption active ingredient-containing pellet for oral administration, said pellet comprising a core of an active ingredient selected from the group consisting of anhydrous theophylline, aminophylline, dyphylline, theophylline calcium salicylate and theophylline sodium glycinate and an organic acid selected from the group consisting of citric acid, tartaric acid, succinic acid, malic acid, ascorbic acid and fumaric acid or a mixture thereof embedded in a polymeric material which contains a major proportion of a water-soluble polymer and a membrane of a film-forming polymer or mixture thereof surrounding the core whereby said active ingredient is released at a controlled rate in an aqueous medium and said pellet has a dissolution rate in an aqueous medium which is substantially independent of pH and which when measured is a basket assembly according to U.S. Pharmacopoeia XX at 37° C. and 75 r.p.m., in a buffer solution at pH 7.5 has the following characteristics:

(a) from 0 to 15% of said active ingredient is released after two hours of measurement in said assembly;

(b) from 15 to 35% of said active ingredient is released after 7 hours of measurement in said assembly;

(c) from 45 to 65% of said active ingredient is released after 13 hours of measurement in said assembly; and (d) from 80 to 100% of said active ingredient is released after 24 hours of measurement in said assembly.

2. A pellet according to claim 1, wherein the active ingredient and organic acid are present in a ratio of 4:1.

3. A pellet according to claim 1, wherein the polymeric material of the core includes a major proportion of a water-soluble polymer selected from hydroxypropylmethylcellulose and polyvinylpyrrolidone.

4. A pellet according to claim 1, wherein the polymeric material of the core consists solely of a water-soluble polymer selected from hydroxypropylmethylcellulose and polyvinylpyrrolidone.

5. A pellet according to claim 3, wherein the polymeric material of the core includes a minor proportion of a water-insoluble polymer selected from the group consisting of methylcellulose, ethylcellulose, propylcellulose and shellac.

6. A pellet according to claim 5, wherein the water-soluble polymer and water-insoluble polymer are present in a ratio of 9:1.

7. A pellet according to claim 1, wherein said active ingredient, organic acid and polymeric material is built up on an inert core.

8. A pellet according to claim 7, wherein the inert core is a non-pareil seed having an average diameter of from 0.3 to 0.7 mm.

9. A pellet according to claim 1, wherein the membrane includes a major proportion of a water-insoluble polymer selected from the group consisting of methylcellulose, ethylcellulose, propylcellulose and shellac.

10. A pellet according to claim 9, wherein the membrane includes a minor proportion of a water-soluble polymer, the ratio of water-insoluble to water-soluble polymer being determined by the inherent solubility characteristics of the polymers selected.

11. A pellet according to claim 10, wherein the membrane consists of ethylcellulose and hydroxypropylmethylcellulose in a ratio of 9:1.

12. A pellet according to claim 10, wherein the membrane consists of a copolymer of acrylic and methacrylic acid esters which is slightly permeable to water and a copolymer of acrylic and methacrylic acid esters which is freely permeable to water in a ratio of 8:2.

13. A pellet according to claim 10, wherein the membrane consists of shellac and polyvinylpyrrolidone in a ratio of 9:1.

14. A capsule comprising pellets according to claim 1.

15. A tablet comprising pellets according to claim 1.

16. A pellet according to claim 1, wherein the polymeric material of the core comprises a major proportion of a copolymer of acrylic and methacrylic acid esters which is freely permeable to water and a minor proportion of a copolymer of acrylic and methacrylic acid esters which is slightly permeable to water.

17. A pellet according to claim 1, wherein the membrane consists of a copolymer of acrylic and methacrylic acid esters which is slightly permeable to water and a copolymer of acrylic and methacrylic acid esters which is freely permeable to water in a ratio of 8:2.

* * * * *

UNITED STATES PATENT AND TRADEMARK OFFICE
CERTIFICATE OF CORRECTION

PATENT NO. : 4,820,521

DATED : April 11, 1989

INVENTOR(S) : Donald E. Panoz, Edward J. Geoghegan

It is certified that error appears in the above-identified patent and that said Letters Patent is hereby corrected as shown below:

Title page [73] - change "Eland" to --Elan--.

Column 4, line 24 - change "dired" to --dried--.

Column 7/8, TABLE 3, under "SUBJ", line "4", in column "10.00", change "1.61" to --11.61--.

Column 9/10, TABLE 4, on SUBJ line, 2nd column, change "4.00" to --3.00--.

Signed and Sealed this

Twenty-second Day of September, 1992

Attest:

DOUGLAS B. COMER

Attesting Officer

Acting Commissioner of Patents and Trademarks